(12) United States Patent
Neuberger et al.

(10) Patent No.: US 6,574,401 B2
(45) Date of Patent: Jun. 3, 2003

(54) OPTICAL FIBER-HANDPIECE COMBINATION FOR MEDICAL LASER TREATMENTS

(75) Inventors: Wolfgang Neuberger, Labuan (MY); Brian Foley, Wilbraham, MA (US)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 10/023,326

(22) Filed: Dec. 17, 2001

(65) Prior Publication Data

US 2002/0064328 A1 May 30, 2002

Related U.S. Application Data

(63) Continuation-in-part of application No. 09/281,536, filed on Mar. 30, 1999, now abandoned.

(51) Int. Cl.[7] .............................. G02B 6/06; A61B 18/18
(52) U.S. Cl. .................... 385/117; 385/147; 606/15; 606/16
(58) Field of Search ................................ 385/115, 116, 385/117, 118, 136, 137, 38, 147, 34, 53, 89; 606/15, 16, 13, 14

(56) References Cited

U.S. PATENT DOCUMENTS

| | | | |
|---|---|---|---|
| 5,304,172 A | | 4/1994 | Manoukian |
| 5,396,880 A | * | 3/1995 | Kagan et al. ............... 600/109 |
| 5,489,205 A | | 2/1996 | Davis |
| 5,951,544 A | * | 9/1999 | Konwitz ....................... 606/16 |
| 5,957,914 A | * | 9/1999 | Cook et al. .................... 606/15 |

OTHER PUBLICATIONS

Michalske, T. and Bunker, B., "The Fracturing of Glass", Scientific American, Dec., 1987, pp. 122–129.

* cited by examiner

Primary Examiner—Euncha Cherry
(74) Attorney, Agent, or Firm—Bolesh J. Skutnik; BJ Associates

(57) ABSTRACT

The present invention describes a multi-component handpiece that is both economical and practical for surgical laser treatment. A disposable optical fiber is inserted into a reusable handpiece. The distal end of the optical fiber is protected by a micro-walled protective tube to prevent the disposable fiber from chipping before and during insertion into the handpiece. Once the optical fiber is protected, it is inserted into the handpiece by threading the optical fiber through the cap, body, and cannula of the handpiece until the fiber extends slightly beyond the distal end of the needle. The micro-walled protective tube is removed from the end of the optical fiber, the optical fiber is positioned, and the cap is tightened. The cap and body of the handpiece cooperate to produce a tight friction fit that prevents longitudinal movement of the optical fiber during laser therapy. The tight friction fit holds the optical fiber in place without the use of adhesives, which allows for facilitated removal of the disposable fiber after use. Furthermore, a disposable fiber allows for convenient resterilization of the handpiece to eliminate the transmission of disease from one patient to the next without having to dispose of the entire handpiece following every laser procedure.

6 Claims, 5 Drawing Sheets

OPTICAL FIBER-HANDPIECE COMBINATION FOR MEDICAL LASER TREATMENTS

REFERENCE TO RELATED APPLICATION

This application is a continuation-in-part of copending U.S. patent application Ser. No. 09/281,536 filed on Mar. 30, 1999, now abandoned, by Wolfgang Neuberger and Brian Foley, inventors, entitled "OPTICAL FIBER-HANDPIECE COMBINATION FOR MEDICAL LASER TREATMENTS", and incorporated by reference herein.

BACKGROUND OF THE INVENTION

1. Field of the Invention

The present invention relates to a multi-component fiber optic handpiece that is particularly safe, practical and economical for use in medical laser treatment.

2. Information Disclosure Statement

An optical fiber handpiece is generally used in ophthalmic, dental, and orthopedic surgical procedures where the treatment area is confined and particularly difficult to reach. Typically, laser light is transmitted from a laser source through an optical fiber to the treatment site. The optical fiber terminates proximally in a laser connector for connection to the laser source and terminates distally in a handpiece, which is manipulated by the surgeon.

As can be appreciated, because of the potential for spreading infection, a handpiece used during one procedure cannot be used with another patient in a subsequent procedure unless some form of sterilization is performed. Unfortunately, the handpieces that were initially introduced to the marketplace were not designed to withstand sterilization procedures and were therefore discarded after use on a single patient. However, this method is not cost-effective.

Since that time, attention has been given to improving the design of the handpiece so that it can be resterilized. Various handpieces have been manufactured and sold which can be resterilized using gas techniques. Unfortunately, gas sterilization is a relatively time consuming and costly approach. In contrast, high temperature steam sterilization in an autoclave is faster and less expensive. However, handpieces were generally incapable of withstanding the high temperatures that are encountered in an autoclave.

U.S. Pat. No. 5,304,172 provides a partial solution to this problem by carefully selecting materials for the handpiece body that can withstand the maximum heat that is encountered in an autoclave, which is about 132 degrees centigrade. However, the optical fibers that are incorporated into the handpiece failed or were damaged during reuse. The disclosed fiber optic probe utilizes a two-piece optic fiber to deliver laser radiation through the handpiece. The two pieces are held in place by spring-biased ferrules that force the mating ends of the fibers together. No means are disclosed to protect the optical fiber during insertion or prior to adhesively securing the optical fibers to the ferrules.

It has been found through research that exposure to the input face of the fiber to the cycling of the pressurized steam occurring during sterilization in an autoclave enhanced and accelerated the formation of cracks in the silica glass at the fiber surface. It has been previously reported that water molecules in the presence of cracks in glass can accelerate the breakdown of bonds. (See, "The Fracturing of Glass," Michalske and Bunker, *Scientific American*, December, 1987, pages 122–129). As can be appreciated, the high temperatures generated in an autoclave can force steam molecules into any microscopic cracks that are present in the fiber, accelerating the breakdown of atomic bonds. It is also believed that when the autoclave is rapidly depressurized, turbulence is created, forcing debris into the input face of the fiber thereby increasing the damage. These cracks and other imperfections lead to breakdown of the fiber during use.

Accordingly, it would be desirable to provide a handpiece that could be sterilized in an autoclave without the complications associated with the prior art.

One possible solution is to remove the optical fiber prior to resterilization. However, the fiber can be damaged during insertion and an adequate means to removably lock the fiber in position would be required. Misalignment of the fiber is prevalent when the fiber is not permanently incorporated into a handpiece device, which can result in damage to the fiber during assembly and actual use of the handpiece.

U.S. Pat. No. 5,489,205 discloses a syringe tip locking assembly comprising means for compressing a handpiece body against a removable syringe. The four part holding mechanism described may work for a metal syringe, but will not necessarily work on a glass fiber. In a holding means such as that disclosed, if the fiber were not perfectly centered prior to being locked in place, it would be possible to lock a fiber with only 3 of the 4 prongs, thereby placing unbalanced forces on the fiber. Stress crazing could result in catastrophic failure of the fiber.

It is therefore an object of the present invention to find a solution to the handpiece-fiber combination that is both economical and practical for medical laser treatment.

OBJECTS AND SUMMARY OF THE INVENTION

It is an object of the present invention to provide a handpiece-fiber combination without the complications associated with the prior art. In particular, a multi-component handpiece is described that is safe, practical and economical for medical laser treatment.

It is another aim of the present invention to provide a means to protect the optical fiber before and during insertion into a handpiece device.

It is a further aim of the present invention to describe a means to prevent longitudinal movement of an optical fiber during surgical laser therapy.

It is an even further aim of the present invention to eliminate the transmission of disease from one patient to the next without having to dispose of the entire handpiece following every laser procedure.

Briefly stated, the present invention describes a multi-component handpiece that is both economical and practical for surgical laser treatment. A disposable optical fiber is inserted into a reusable handpiece. The distal end of the optical fiber is protected by a micro-walled protective tube to prevent the disposable fiber from chipping before and during insertion into the handpiece. Once the optical fiber is protected, it is inserted into the handpiece by threading the optical fiber through the cap, body, and needle cannula of the handpiece until the fiber extends slightly beyond the distal end of the cannula. The micro-walled protective tube is removed from the end of the optical fiber, the optical fiber is positioned, and the cap is tightened. The cap and body of the handpiece cooperate to produce a tight friction fit that prevents longitudinal movement of the optical fiber. The tight friction fit holds the optical fiber in place without the use of adhesives to eliminate the problem of residual glue on the handpiece device and to allow for facilitated removal of the disposable fiber after use. Furthermore, a disposable fiber allows for convenient resterilization of the handpiece, eliminating the transmission of disease from one patient to the next without having to dispose of the entire handpiece following every laser procedure.

The above and other objects, features and advantages of the present invention will become apparent from the following detailed description read in conjunction with the accompanying drawings.

BRIEF DESCRIPTION OF THE DRAWINGS

FIG. 3a an illustration of the body of the handpiece,

FIG. 3b a cross-section of the distal end of the body;

FIG. 3c a cross-section of the proximate end of the handpiece body.

FIG. 5a a straight cannula

FIG. 5b a series of various bend angles of the cannula.

DESCRIPTION OF PREFERRED EMBODIMENTS

The present invention describes a multi-component handpiece that is safe, practical, and economical for surgical laser treatment. The present invention may be used with any suitable high brightness source such as laser diodes, frequency-double laser diodes, diode pumped solid state lasers, frequency doubled diode pumped solid state lasers, diode pumped fiber lasers, super luminescent diodes and light emitting diodes of high brightness without departing from the scope of the present invention.

Figure 1:
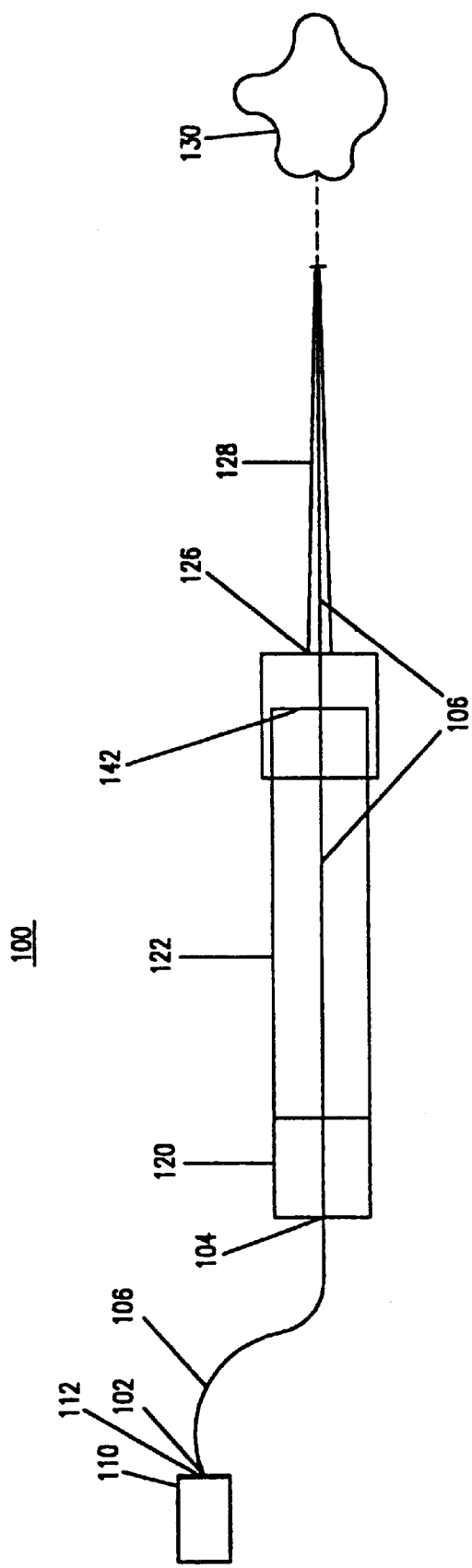
FIG. 1 shows a preferred embodiment of a multi-component handpiece used in connection with a laser assembly.

FIG. 1 shows a preferred embodiment of multi-component handpiece 100 used in connection with a laser assembly. Handpiece 100 consists of five components: reusable body 122, disposable optical fiber 106, cap 120, cannula 128, and micro-walled protective tube 142.

Proximate end 102 of disposable fiber 106 is connected to laser source 110 at laser connector point 112. Distal end 126 of optical fiber 106 is protected by micro-walled protective tube 142 to prevent chipping of disposable fiber 106 before and during insertion into handpiece 100. Micro-walled protective tube 142 is made of a non-metallic substance that will not scratch or damage disposable optical fiber 106. Disposable fiber 106, protected by micro-walled protective tube 142, is inserted into handpiece 100 by threading optical fiber 106 through fiber insertion point 104 of cap 120. Fiber 106 is then pushed through body 122 and through cannula 128. Fiber 106 extends slightly beyond the distal end of cannula 128. Micro-walled protective tube 142 is removed and cap 120 is tightened to prevent longitudinal movement of optical fiber 106.

Figure 2:
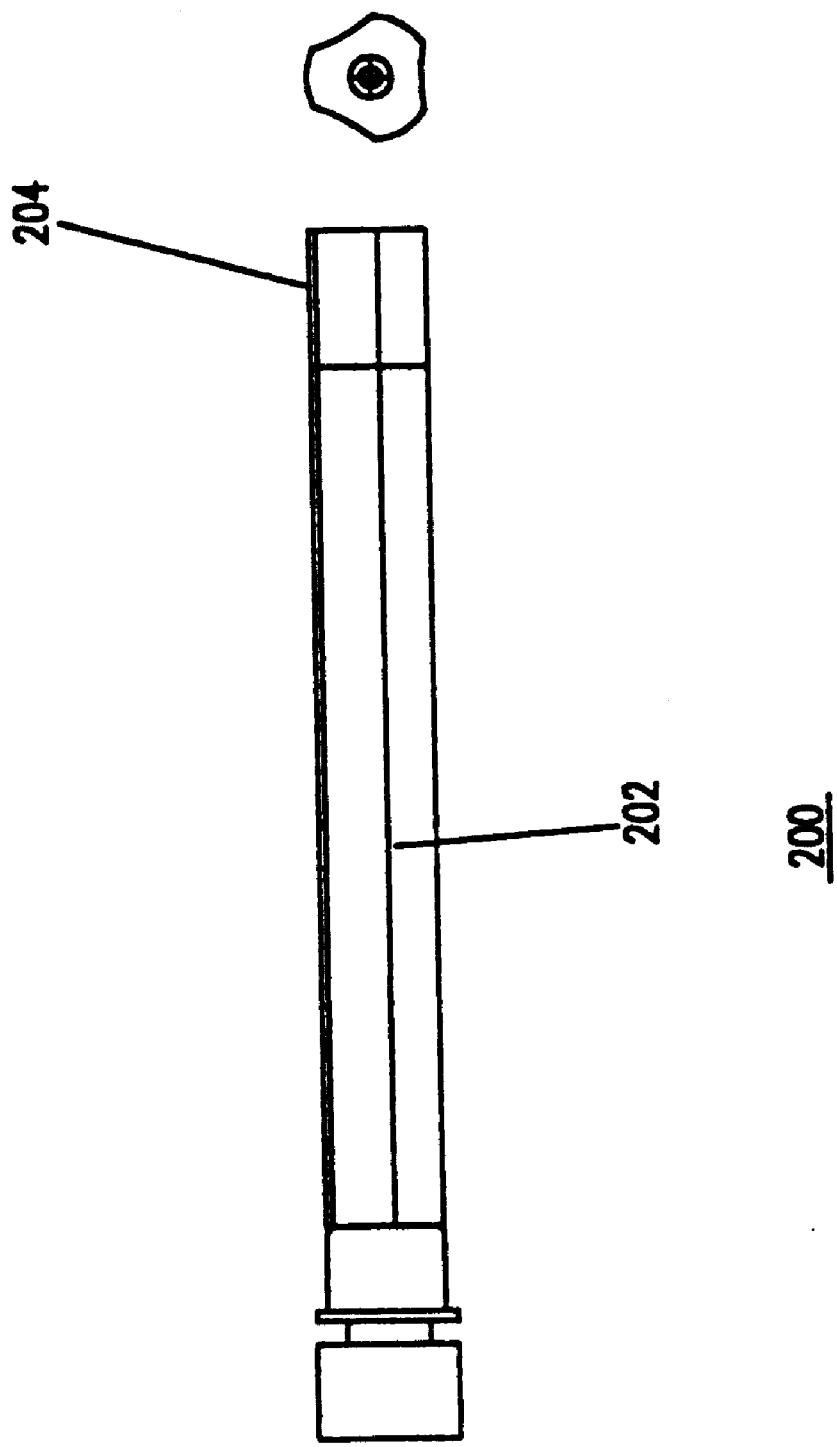
FIG. 2 shows the distal end of an optical fiber protected by a micro-walled protective tube.

FIG. 2 shows the distal end of optical fiber 202 protected by micro-walled protective tube 204. Protective tube 204 protects optical fiber 202 from chipping while optical fiber 202 is inserted into an optical fiber handpiece. In a preferred embodiment, protective tube 204 is made out of polyimide. One of ordinary skill in the art, in light of the teachings herein, can readily use different materials for protective tube 204 without exceeding the scope of the present invention.

In a preferred embodiment, optical fiber 202 is disposable to facilitate resterilization of the handpiece. A disposable fiber is advantageous because it allows the handpiece to be resterilized by steam without the complications associated with the prior art. Furthermore, a disposable fiber is preferred because steam sterilization of optical fiber 202 may lead to degradation of the fiber's coating or to fatigue, which may result in premature breakage.

Replacement fibers may be provided with a micro-walled protective tube pre-attached. Alternatively, replacement fibers and protective tubes may be obtained separately and a sterilized protective tube can be placed on the distal end of the fiber in a sterile environment prior to refitting the handpiece.

Figure 3:
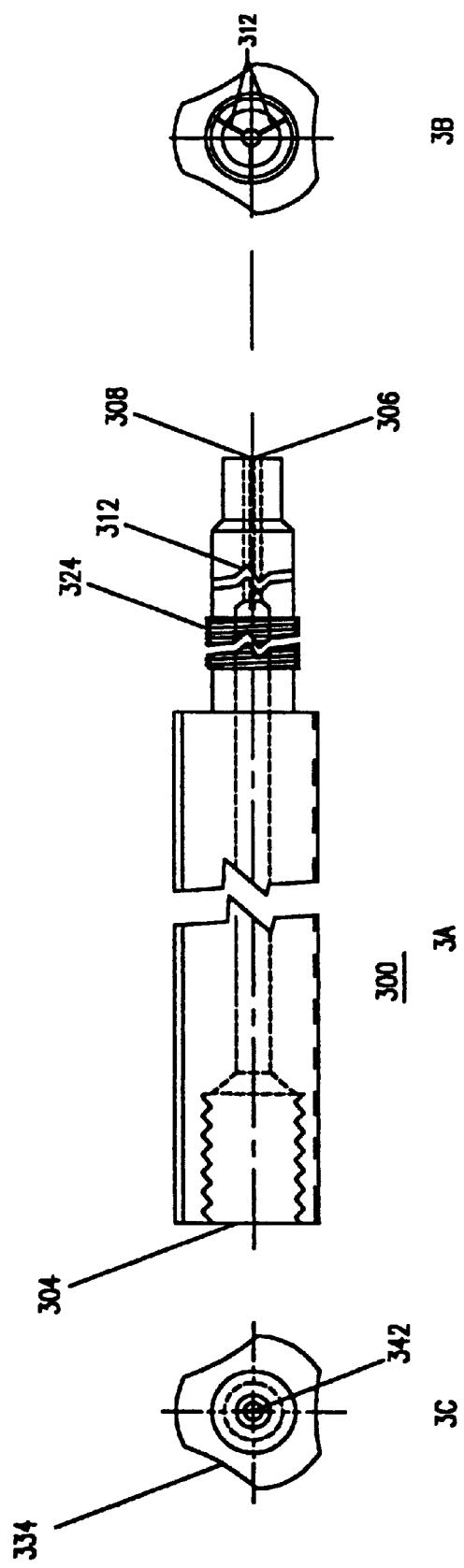
FIG. 3 illustrates a sectional view of handpiece body, including.

FIG. 3 illustrates a sectional view of handpiece body 300. Slits 312 are provided at proximate end 306 of body 300. Threaded portion 324 is located immediately adjacent to slits 312. The purpose of slits 312 and threaded portion 324 will become apparent in the subsequent description.

Figure 4:
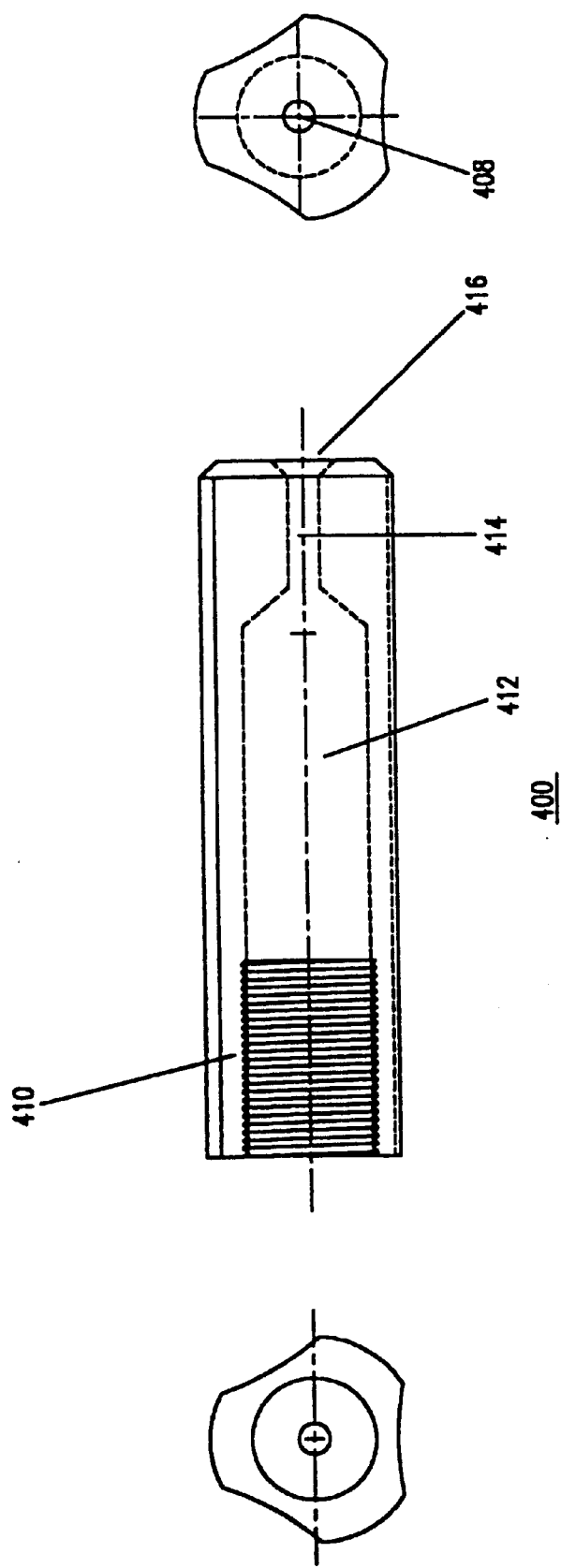
FIG. 4 is an illustration of the cap.

FIG. 4 illustrates a sectional view of cap 400. Cap 400 has an internally threaded portion 410 that engages the threaded portion 324 of body 300. A cylindrical recess 412 in cap 400 is dimensioned to fit around proximate end 306 of body 300, while entry channel 414, which is slightly larger in diameter than the optical fiber, is provided at opposite end 416 of cap 400 to slidably position the optical fiber.

With further reference to FIGS. 3 and 4, the cooperation between cap 400 and body 300 prevents longitudinal movement of an optical fiber during laser therapy. With particular reference to FIG. 3b, proximate end 306 of body 300 has three slits 312 spaced 120° apart. Slits 312 prevent longitudinal movement of the optical fiber during laser therapy. The use of three slits spaced equidistantly allows the optical fiber (not shown) to be guided to the center of the handpiece before the fiber is locked in place. If a 4 slit holding means were used, it would be possible to lock the fiber in the device before the fiber was centered. Unbalanced forces on the fiber could cause stress crazing and failure of the optical fiber.

Still referring to FIGS. 3 and 4, the optical fiber is slipped through thru-hole 408 in cap 400 and into body 300 through fiber insertion end 308. Threaded portion 410 of cap 400 threadably engages the threaded portion 324 of body 300 in a conventional fashion. Upon tightening, cap 400 compresses the slits on proximate end 306 of body 300 that simultaneously compresses proximate end 306 of body 300 against the optical fiber. Upon doing so, cap 400, body 300, and an optical fiber are locked against longitudinal movement with respect to each other. The optical fiber can be removed from the handpiece simply by loosening cap 400 and withdrawing the optical fiber from body 300.

As another example, a wedge device may be positioned on the exterior of the device to apply pressure to the fiber to prevent misalignment during laser surgery. Additionally, a stop point may be designed to prevent the fiber from being pushed all the way through the handpiece device and adhesives may be used to further prevent misalignment of the fiber without exceeding the scope of the present invention.

With particular reference to FIG. 3, distal end 304 and proximate end 306 of body 300 were designed to enhance mechanical gripping of the handpiece. Instead of using the conventional circular shape for the ends, grooves 334 were cut to fit the fingers comfortably.

Figure 5:
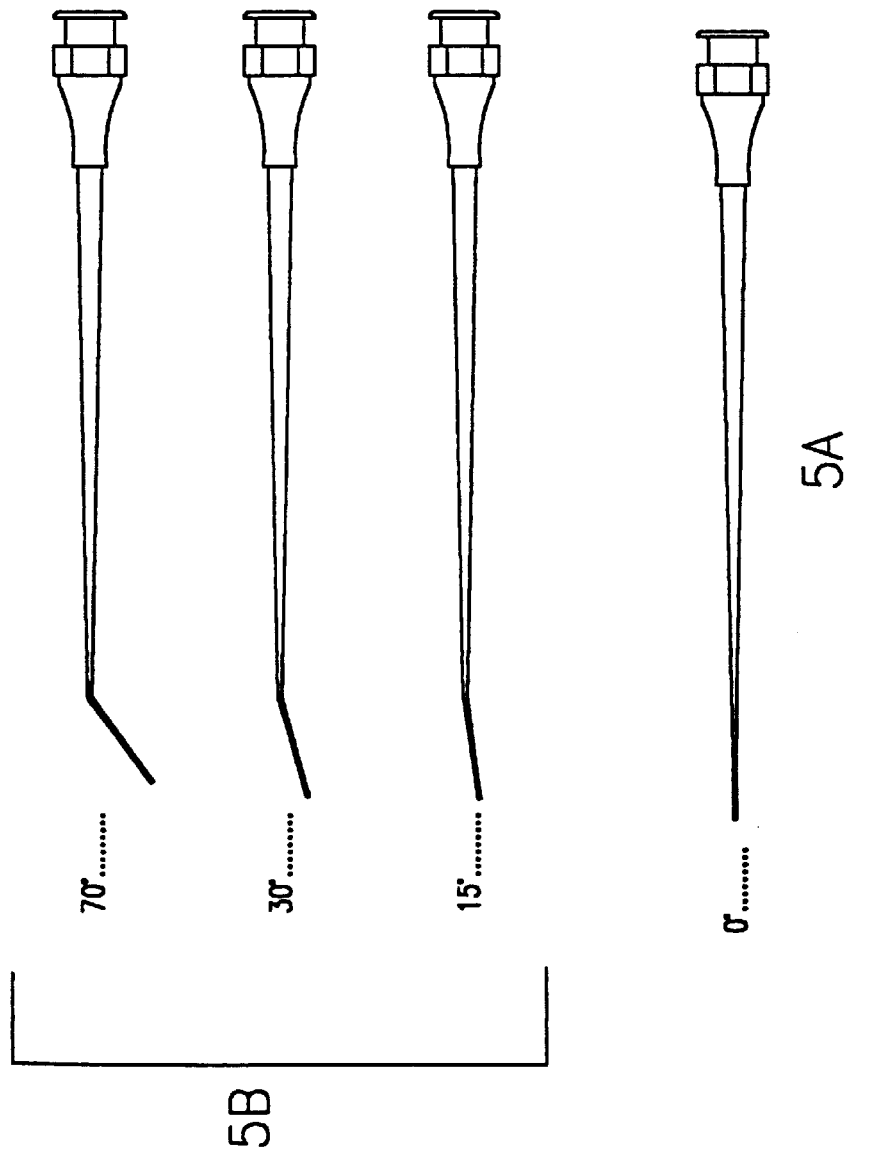
FIG. 5 is an illustration of several styles of cannula.

With reference to FIG. 3, a cannula is inserted at distal end 304 of body 300 at needle insertion point 342. FIG. 5 is an illustration of cannula 500. Cannula 500 may be resterilized. In a preferred embodiment cannula 500 is made out of stainless steel. One of ordinary skill in the art, in light of the teachings herein, can readily use different materials for cannula 500 without departing from the scope of the present invention.

FIG. 5, subfigure 5b is an illustration of the various bend angles of cannula 500 which typically range from 0° to 70°. A straight needle cannula may be advantageous to reach a treatment site that is deep within the body cavity. Whereas a needle cannula with a 70° bend may be advantageous for procedures in which the treatment site is particularly confined and difficult to reach.

A 70° angle is typically the most severe angle that is used to avoid concerns about damaging the fiber inside cannula 500. A fiber that is placed in a sharply bent needle may result in a loss of power density at the treatment site. Additionally, stress on the outer diameter of the fiber may lead to fatigue.

A package of replacement needles may be purchased with differing bend angles to perform various surgical laser procedures. Alternatively, a package of replacement cannulas with the same bend angle may be purchased for routine surgical laser treatments that only require one specific bend angle to reach the treatment site.

Certain changes may be made in the above constructions without departing from the scope of the invention, it is intended that all matter contained in the above description and shown in the accompanying drawings be considered as illustrative and not in a limiting sense. For example, various high brightness light sources may be used in conjunction with the present invention which may include, but is not limited to laser diodes, frequency-double laser diodes, diode pumped solid state lasers, frequency doubled diode pumped solid state lasers, diode pumped fiber lasers, super luminescent diodes and light emitting diodes of high brightness without departing from the scope of the present invention.

Having described the preferred embodiments of the invention with reference to the accompanying drawings, it is to be understood that the present invention is not limited to these precise embodiments, and that various changes and modifications may be effected therein by one skilled in the art without departing from the scope or spirit of the invention as defined in the appended claims.

What is claimed is:

1. A multi-component handpiece device for use with a laser assembly comprising:

an optical fiber, a micro-walled protective tube, a handpiece, and a cannula;

wherein said handpiece device has means for removably locking said optical fiber to said handpiece;

wherein a distal end of said optical fiber is temporarily protected prior to and during insertion into said handpiece by said micro-walled protective tube; and wherein said micro-walled protective tube is removed to expose said distal end of said optical fiber before said means for removably locking said optical fiber to said handpiece is engaged.

2. A device according to claim 1, wherein said micro-walled protective tube is made of polyimide.

3. A device according to claim 1, wherein said cannula is made of stainless steel.

4. A device according to claim 1, wherein said locking means for removably locking said optical fiber to said handpiece comprises means for compressing a proximate end of said handpiece body against said optical fiber.

5. A device according to claim 4, wherein said proximate end of said body comprises three slits spaced 120° apart.

6. A method of use according to the device in claim 1 comprising the steps of:

protecting said distal end of said optical fiber by enclosing said distal end of said optical fiber in said micro-walled protective tube;

inserting said tube protected distal end of said fiber into a proximal end of said handpiece device and through said cannula;

removing said micro-walled protective tube from said distal end of said fiber;

engaging said means for removably locking said optical fiber to said handpiece to prevent longitudinal movement of said optical fiber;

irradiating a preselected treatment site;

removing said fiber and discarding it; and resterilizing said handpiece device and cannula with no fiber present.

* * * * *